United States Patent
Nokita et al.

(10) Patent No.: US 7,382,859 B2
(45) Date of Patent: Jun. 3, 2008

(54) X-RAY IMAGING APPARATUS AND METHOD

(75) Inventors: Makoto Nokita, Tochigi (JP); Osamu Tsujii, Tochigi (JP)

(73) Assignee: Canon Kabushiki Kaisha, Shimomaruko Ohta-ku, Tokyo (JP)

( * ) Notice: Subject to any disclaimer, the term of this patent is extended or adjusted under 35 U.S.C. 154(b) by 129 days.

(21) Appl. No.: 10/873,796

(22) Filed: Jun. 22, 2004

(65) Prior Publication Data

US 2004/0258204 A1   Dec. 23, 2004

(30) Foreign Application Priority Data

Jun. 23, 2003   (JP)   ............... 2003-178605

(51) Int. Cl.
*H05G 1/64* (2006.01)
*H05G 1/08* (2006.01)
*G01T 1/24* (2006.01)

(52) U.S. Cl. .................. 378/98.8; 378/91; 250/370.09
(58) Field of Classification Search ............... 378/98.8, 378/91, 114, 115, 116, 117, 189, 190, 191; 250/370.09
See application file for complete search history.

(56) References Cited

U.S. PATENT DOCUMENTS

| | | | | |
|---|---|---|---|---|
| 5,661,309 A | * | 8/1997 | Jeromin et al. ............. | 250/580 |
| 5,844,961 A | * | 12/1998 | McEvoy et al. ............ | 378/98.8 |
| 5,877,501 A | * | 3/1999 | Ivan et al. ............. | 250/370.09 |
| 5,886,359 A | * | 3/1999 | Bringley et al. ............ | 250/580 |
| 6,163,386 A | * | 12/2000 | Kobayashi et al. ......... | 358/482 |
| 6,307,915 B1 | * | 10/2001 | Frojdh ........................ | 378/98.8 |
| 6,459,765 B1 | * | 10/2002 | Ganin et al. ................ | 378/108 |
| 6,469,312 B2 | * | 10/2002 | Agano ........................ | 250/580 |
| 6,510,202 B2 | * | 1/2003 | Tamura et al. .............. | 378/155 |
| 6,714,623 B2 | | 3/2004 | Sako et al. ................ | 378/98.8 |
| 6,801,594 B1 | * | 10/2004 | Ali et al. ........................ | 378/4 |
| 6,806,473 B2 | * | 10/2004 | Honda et al. .......... | 250/370.11 |
| 7,239,685 B2 | * | 7/2007 | Petrick et al. .............. | 378/116 |

FOREIGN PATENT DOCUMENTS

JP   8-116044   5/1996
JP   2000-139889   5/2000

OTHER PUBLICATIONS

Patents Abstract of Japan English Abstract for JP 2000-139889.
Search Report for corresponding Korean Patent Application No. 10-2004-0046988.

* cited by examiner

*Primary Examiner*—Allen C. Ho
(74) *Attorney, Agent, or Firm*—Morgan & Finnegan, L.L.P.

(57) ABSTRACT

Since a notification unit (130) notifies a radiographer of the driving state of an X-ray detector (110), he/she can identify that the X-ray detector (110) is set in a detection signal accumulation state. When the irradiation button of an X-ray generation apparatus is then pressed, a subject can be irradiated with X-rays.

13 Claims, 12 Drawing Sheets

X-RAY IMAGING APPARATUS AND METHOD

FIELD OF THE INVENTION

The present invention relates to an X-ray imaging apparatus and method which require no synchronization with the X-ray generation timing in executing X-ray imaging in, for example, a medical facility and, more particularly, to an X-ray imaging apparatus and method using an X-ray detector capable of directly converting an X-ray image into a digital output in real time.

BACKGROUND OF THE INVENTION

Conventional X-ray sensors used to acquire an X-ray image of a person to be examined in X-ray imaging include Film/Screen systems (to be referred to as F/Ss hereinafter) which are formed by inserting a film and an intensifying screen into a cassette and Imaging Plates (to be referred to as IPs hereinafter) which are put in cassettes and used in computed radiography. X-ray sensors of these types need not be synchronized with the X-ray generation timing. A radiographer can acquire X-ray images without any blur caused by the motion of internal organs or body while observing only the breathing state and motion of the person to be examined. Hence, the X-ray generation apparatus is designed to irradiate a subject with X-rays with a delay of several ten ms to several hundred ms at the latest after the X-ray irradiation button is pressed.

In recent years, X-ray sensors capable of directly converting an X-ray image into a digital output in real time have been proposed. A solid-state photodetector can be manufactured by forming an amorphous semiconductor on, for example, a silica glass substrate and arraying solid-state photodetection elements each including a transparent conductive film and a conductive film in a matrix on the amorphous semiconductor. An X-ray detector is formed by stacking such a solid-state photodetector and a scintillator which converts X-rays into visible light.

When this X-ray detector is used, an X-ray digital image is acquired by the following process.

The X-ray detector is irradiated with X-rays that have passed through a subject. The X-rays are converted into visible light by the scintillator. The visible light is detected as an electrical signal by the photoelectric conversion unit of each solid-state photodetection element.

The electrical signal is read out from each solid-state photodetection element by a predetermined read method and A/D-converted so that an X-ray image signal is obtained.

The X-ray detector is described in detail in, for example, Japanese Patent Laid-Open No. 8-116044. There are also a number of detectors proposed, which cause a solid-state photodetector to acquire X-rays directly without using any scintillator.

Such an X-ray sensor capable of directly converting an X-ray image into a digital output in real time will be referred to as an X-ray detector hereinafter.

These X-ray detectors detect an X-ray intensity as a charge amount. To accurately accumulate the X-ray detection signal, these X-ray detectors require driving with a predetermined cycle for X-ray image acquisition, including charge removal from pixels, idling for stabilizing the potential between the pixels, charge accumulation for accumulating the X-ray detection signal, and charge read from the pixels.

The time of the charge accumulation state by the X-ray detector is limited. To irradiate the X-ray detector with X-rays in its accumulation state, the X-ray generation apparatus and the X-ray detector are synchronized with each other. More specifically, the X-ray detector is driven such that it has a plurality of driving states including charge removal from pixels, idling, and charge accumulation when the X-ray irradiation button is pressed. As soon as the X-ray detector is set in the accumulation state, an X-ray irradiation signal is transmitted to the X-ray generation apparatus to irradiate a subject with X-rays.

However, when a subject is irradiated with X-rays after driving necessary for accumulation in the X-ray detector is executed in synchronism with the X-ray irradiation button, the delay after the radiographer presses the X-ray irradiation button until actual X-ray irradiation becomes longer than a normal case without synchronization. It is therefore difficult to acquire an X-ray image without any blur caused by the motion of internal organs or body.

SUMMARY OF THE INVENTION

The present invention has been made in consideration of the above problem, and has as its object to provide an X-ray imaging apparatus and method which require no synchronization with the X-ray generation timing.

In order to solve the above-described problem and achieve the above object, according to the present invention, there is provided an X-ray imaging apparatus comprising an X-ray detector which detects X-rays emitted from an X-ray source, a detector control unit which drives and controls the X-ray detector, and a notification unit which notifies a radiographer of a driving state of the X-ray detector.

According to the present invention, there is also provided an X-ray imaging method by using an X-ray imaging apparatus comprising an X-ray detector which detects X-rays emitted from an X-ray source, and a detector control unit which drives and controls the X-ray detector, comprising detecting a plurality of driving states of the X-ray detector and distinguishably notifying a radiographer of each driving state.

As described above, according to the first aspect, since the radiographer is notified of the driving state of the X-ray detector, he/she can identify that the X-ray detector is set in the accumulation state. After that, the irradiation button of an X-ray generation apparatus is pressed to irradiate a subject with X-rays. Accordingly, synchronization between the X-ray detector and the X-ray generation apparatus is unnecessary. Hence, the radiographer can carry the X-ray detector and execute imaging without minding connection. In addition, when the irradiation button of the X-ray generation apparatus is pressed to irradiate a subject with X-rays, due to the delay of X-ray irradiation caused by the time required for driving necessary after the irradiation button is pressed until the X-ray detector is set in the accumulation state, a blur due to the motion of the subject and, for example, a blur around the heart caused by its motion can be eliminated.

According to the second aspect, since the radiographer is notified of both the signal accumulation state in which X-ray irradiation is possible and a read state in which X-ray irradiation is impossible, an appropriate X-ray image can be obtained.

According to the third aspect, since the start and end of X-ray irradiation are detected, the X-ray detector can be driven in accordance with the timing of X-ray irradiation.

Hence, an X-ray image can accurately quickly be acquired without any wasteful driving.

According to the fourth aspect, a detector used for the X-ray irradiation detection unit and the X-ray detector which acquires an X-ray image are separately prepared. For this reason, detectors specialized for their roles can be used, and high performance and accuracy can be obtained.

According to the fifth aspect, a detector used for the X-ray irradiation detection unit and the X-ray detector which acquires an X-ray image are separately prepared. For this reason, detectors specialized for their roles can be used, and high performance and accuracy can be obtained.

According to the sixth aspect, an uncorrected X-ray image is an image obtained from the sum of offset charges by a dark current and signal charges by X-rays. The magnitude of the offset charges by the dark current is determined by accumulation time. When the accumulation time of the signal charges by the X-rays equals the accumulation time of the correction image, an X-ray image almost free from offset charges caused by the difference can be obtained.

For example, a radiographer presses the X-ray irradiation button while observing only the motion or breathing of a patient. According to an X-ray imaging apparatus of the seventh aspect, the radiographer can grasp the driving state of the X-ray detector on the basis of sound so that he/she can execute imaging while concentrating on only the motion of the patient.

A radiographer presses the X-ray irradiation button while observing only the motion or breathing of a patient. According to an X-ray imaging apparatus of the eighth aspect, the radiographer can grasp the driving state of the X-ray detector by holding the vibration source in a hand so that he/she can execute imaging while concentrating on only the motion of the patient.

According to the ninth aspect, since the driving state of the X-ray detector can be displayed on, for example, the OPU without connecting it by a wire, the portability of the X-ray imaging apparatus can be increased.

A radiographer presses the X-ray irradiation button while observing only the motion or breathing of a patient. According to an X-ray imaging apparatus of the 10th aspect, the radiographer can grasp the driving state of the X-ray detector by holding the vibration source in a hand so that he/she can execute imaging while concentrating on only the motion of the patient.

A radiographer presses the X-ray irradiation button while observing only the motion or breathing of a patient. According to an X-ray imaging apparatus of the 11th aspect, the radiographer can grasp the driving state of the X-ray detector on the basis of light emitted from a housing of the X-ray detector. Hence, he/she can execute imaging while simultaneously observing the motion of the patient who is in contact with the housing of the X-ray detector.

Driving of the X-ray detector is started by pressing the X-ray irradiation button. According to an X-ray imaging apparatus of the 12th aspect, driving of the X-ray detector can be started by pressing a driving start unit. For this reason, synchronization with an X-ray generation apparatus is unnecessary, and the portability of the X-ray imaging apparatus can be increased.

According to the 13th aspect, the X-ray detector can stabilize by idling driving. Simultaneously with X-ray irradiation, the X-ray detector can stop idling driving and shift to the accumulation state. Hence, a stable X-ray image can be acquired.

According to an X-ray imaging apparatus of the 14th aspect, since driving of the X-ray detector is ended upon detecting the end of X-ray irradiation, wasteful driving can be prevented, and power consumption can be reduced.

According to an X-ray imaging apparatus of the 15th aspect, even for an X-ray detector which must drop the application voltage to reset accumulated charges in the pixels once the accumulation state is set, and therefore, cannot continuously be set in the accumulation state, synchronization with an X-ray generation apparatus is unnecessary.

According to an X-ray imaging apparatus of the 16th aspect, since the radiographer is distinguishably notified of both the accumulation state of the X-ray detector, in which X-ray irradiation is possible, and an accumulation preparation driving state in which X-ray irradiation is impossible, an appropriate X-ray image can be obtained.

According to an X-ray imaging method of the 17th aspect, since the radiographer is distinguishably notified of both the accumulation state of the X-ray detector, in which X-ray irradiation is possible, and an accumulation preparation driving state in which X-ray irradiation is impossible, an appropriate X-ray image can be obtained.

Other subjects and advantages besides those discussed above shall be apparent to those skilled in the art from the description of a preferred embodiment of the invention which follows. In the description, reference is made to accompanying drawings, which form a part hereof, and which illustrate an example of the invention. Such example, however, is not exhaustive of the various embodiments of the invention, and therefore reference is made to the claims which follow the description for determining the scope of the invention.

DETAILED DESCRIPTION OF THE PREFERRED EMBODIMENTS

The preferred embodiments of the present invention will be described below with reference to the accompanying drawings.

First Embodiment

The first embodiment will be described, in which an X-ray imaging apparatus has a notification unit which notifies a radiographer of the driving state of the X-ray detector so that the radiographer can execute imaging without synchronization with the X-ray generation apparatus.

Figure 1:
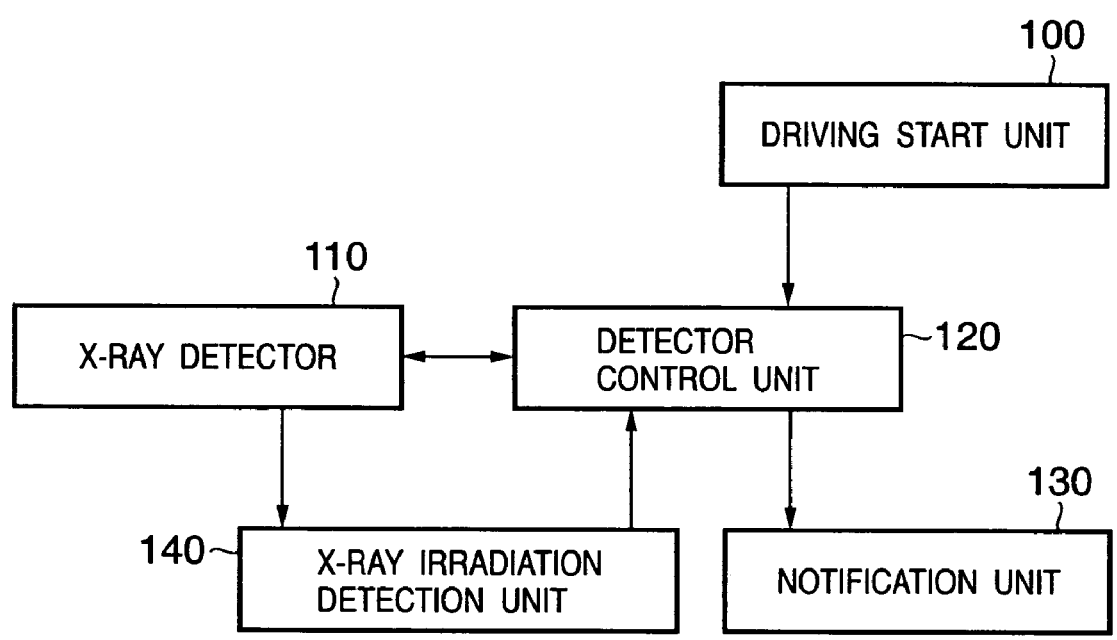
FIG. 1 is a schematic block diagram showing a preferred example of an X-ray imaging apparatus according to the first embodiment.

FIG. 1 is a schematic block diagram showing a preferred example of an X-ray imaging apparatus according to the first embodiment.

Referring to FIG. 1, reference numeral 100 denotes a driving start unit (including a device, circuit, program code, and the like, which have the function); 110, an X-ray detector; 120, a detector control unit (including a device, circuit, program code, and the like, which have the function); 130, a notification unit (including a device, circuit, program code, and the like, which have the function); and 140, an X-ray irradiation detection unit (including a device, circuit, program code, and the like, which have the function). The driving start unit 100 sets the X-ray detector 110 in an imaging enable state.

More specifically, the X-ray detector 110 is powered on, and in this state, driving of the X-ray detector 110 necessary for imaging is started. This operation is generally implemented by, for example, causing the radiographer to press the imaging button on the OPU (OPeration Unit) that operates the X-ray detector 110. The X-ray detector 110 that has started driving is caused to execute predetermined driving operations by the detector control unit 120 until X-ray irradiation.

The driving operations include driving for stabilizing the X-ray detector 110 after voltage application and driving in a state in which the X-ray detector 110 accumulates an X-ray signal with which a subject is irradiated. To make the radiographer recognize the driving (to be referred to as an accumulation state hereinafter) for accumulating the X-ray signal and other driving operations, the notification unit 130 generates a distinguishable signal.

The signal may be a signal by light, a signal by sound, or a signal by vibration. When a signal by light is used, an LED prepared on the housing of the X-ray detector 110 is caused to continuously emit light in the X-ray signal accumulation state and blink in another driving state. Alternatively, a notification of the accumulation state may be displayed on the OPU operated by the radiographer. When a signal by sound is used, the X-ray detector 110 or OPU generates continuous sound in the accumulation state and intermittent sound in another driving state. When a signal by vibration is used, the radiographer carries a portable monitor capable of communicating with the detector control unit 120 so that he/she can know the accumulation state on the basis of the vibration strength.

When it is notified by the notification unit 130 that the X-ray detector 110 is set in the accumulation state, and the irradiation button of the X-ray generation apparatus is pressed (automatically or by the radiographer who has recognized the notification), a subject is irradiated with X-rays. The X-ray signal that has passed through the subject is accumulated by the X-ray detector 110. The X-ray irradiation detection unit 140 time-serially detects X-ray irradiation on the X-ray detector 110 and acquires the irradiation start time when the X-ray detector 110 is irradiated with the X-rays and the irradiation end time.

The X-ray irradiation detection unit 140 may cause a detector different from the X-ray detector 110 to time-serially detect X-ray irradiation. Alternatively, a nondestructive read circuit may be prepared in the X-ray detector 110 to time-serially detect X-ray irradiation by nondestructive read. An example of the detector different from the X-ray detector 110 is a detector used for AEC (Auto Exposure Control) of the X-ray generation apparatus.

The detector control unit 120 executes driving operations for ending the accumulation state of the X-ray detector 110, acquiring correction data, dropping the voltage, and the like on the basis of the acquired irradiation start time and irradiation end time.

As described above, since the radiographer is notified of the driving state of the X-ray detector 110, he/she can identify that the X-ray detector 110 is in the accumulation state. Then, during the accumulation state, the irradiation button of the X-ray generation apparatus is pressed to irradiate a subject with X-rays. Hence, the X-ray detector 110 need not synchronize with the X-ray generation apparatus. Accordingly, the radiographer can carry the X-ray detector 110 and execute imaging without minding connection.

The radiographer presses the irradiation button of the X-ray generation apparatus to irradiate a subject with X-rays after confirming the accumulation state and also the state of the subject. Due to the delay of X-ray irradiation caused by the time required for driving necessary until the X-ray detector 110 is set in the accumulation state, a blur due to the motion of a subject and, for example, an image blur caused by a bodily motion of a subject such as an infant who moves lively can be eliminated. In imaging while observing the heartbeat, a blur around the heart caused by its motion can be eliminated.

The arrangement of the X-ray detector 110 described in FIG. 1 and driving necessary for accumulating and reading out the X-ray signal will be described with reference to FIG. 2.

As the X-ray detector 110, an X-ray detector which directly detects X-rays or an X-ray detector which temporarily converts X-rays into visible light through phosphor and detects the visible light can be used. Either X-ray detector is formed by combining pixels for detecting signals in an array. This is called a detector array. Reference numeral 200 denotes a detector array.

A pixel 201 includes a signal detection unit which detects one X-ray or optical signal and a switching TFT which switches between accumulation and read of the signal. Photoelectric conversion elements PD(1,1) to PD(4096, 4096) correspond to signal detection units. Switches SW(1, 1) to SW(4096,4096) correspond to switching TFTs. These elements will be referred to as photoelectric conversion elements PD(m,n) and switches SW(m,n) hereinafter in correspondence with m (rows)×n (columns) pixels. G (electrode) and D (electrode) respectively represent the gate electrode and common electrode of the photoelectric conversion element PD(m,n). Charges are accumulated or removed by applying different voltages to the electrodes. The photoelectric conversion unit of the photoelectric conversion element PD(m,n) is connected to the gate electrode G via an insulator. The photoelectric conversion unit of the photoelectric conversion element PD(m,n) is also connected to the common electrode D via a semiconductor. Reference symbol Lcm denotes a column signal line of the mth column; Lrn, a row select line of the nth row; and Lb, a bias wiring line. Reference numeral 205 denotes a bias power supply.

The gate electrodes G are connected to the column signal line Lcm common to the column through the corresponding switches SW(m,n). The control terminals of the switches SW(m,n) are connected to the common row select line Lrn. The common electrodes D of all the photoelectric conversion elements PD(1,1) to PD(4096,4096) are connected to the bias power supply 205 through the bias wiring line Lb.

A line selector 232 selects the row of pixels 201 from which signal charges are to be read out. Row select lines Lr1 to Lr4096 are connected to the line selector 232. An address decoder 234 decodes a control signal for the detector control unit 120 to decide the line of photoelectric conversion elements PD(m,n) from which signal charges are to be read out. Switch elements 236 are turned on/off in accordance with the output from the address decoder 234. The line selector 232 includes the address decoder 234 and 4,096 switch elements 236-1 to 236-4096.

A signal read circuit 240 reads out signal charges from the pixels 201. A reset reference potential 241 resets the accumulated charges in the photoelectric conversion elements PD(m,n). The voltage of the reset reference potential 241 is Vb. Reference numeral 242 denotes a reset switch. Each preamplifier 246 amplifies a signal potential from the corresponding column signal line Lcm. Each sample-and-hold circuit 248 samples and holds the output from a corresponding one of the preamplifiers 246. An analog multiplexer 250 multiplexes the outputs from the sample-and-hold circuits 248 along the time axis. An A/D converter 252 converts the analog output from the analog multiplexer 250 into a digital signal. A driver 262 actually drives the X-ray detector 110.

Most basic driving operations in the X-ray detector 110, including refresh (removal of accumulated charges) of the photoelectric conversion elements, charge accumulation, charge read, and pre-read, will be described below. Refresh is necessary/unnecessary depending on the structure of the photoelectric conversion element. An example of the photoelectric conversion element structure that requires refresh is a MIS structure.

Refresh of the photoelectric conversion elements will be described first.

The driver 262 sets the potential of all the common electrodes D connected to the bias wiring line to a refresh potential Vr by applying a voltage to the bias power supply 205. In addition, the driver 262 turns on all the reset switches 242 to connect all the column signal lines Lc1 to Lc4096 to the reset reference potential 241 Vbt. The driver 262 also turns on all the switches SW(1,1) to SW(4096,4096) by applying a potential Vgh to all the row select lines Lr1 to Lr4096, thereby setting the potentials of all the gate electrodes G to Vbt. Accordingly, by the potential difference Vbt−Vr between the potential Vbt of the gate electrodes G and the potential Vr of the common electrodes D, extra charges in the photoelectric conversion elements PD(1,1) to PD(4096,4096) are removed from the common electrodes D so that the photoelectric conversion elements are refreshed.

Charge accumulation will be described next.

The driver 262 sets the potentials of all the common electrodes D connected to the bias wiring line to a bias potential Vs at the time of photoelectric conversion by changing the voltage of the bias power supply 205.

In the state in which the potentials of all the common electrodes D are set to the bias potential Vs at the time of photoelectric conversion, the driver 262 turns on all the reset switches 242 to set all the column signal lines Lc1 to Lc4096 to the reset reference potential 241 Vbt. In addition, all the switches SW(1,1) to SW(4096,4096) are turned on to set the potentials of all the gate electrodes G to Vbt.

In addition, the driver 262 turns off all the reset switches 242 to release all the column signal lines Lc1 to Lc4096 from the reset reference potential 241 Vbt.

The driver 262 also turns off all the switches SW(1,1) to SW(4096,4096) by applying the potential Vgl to all the row select lines Lr1 to Lr4096. The gate electrodes G are insulated from the photoelectric conversion elements PD(1,1) to PD(4096,4096). The common electrodes D and photoelectric conversion elements PD(1,1) to PD(4096,4096) are rendered semiconductive. For these reasons, when the magnitude relationship between the potential of the gate electrode G and the potential Vs of the common electrode D is reversed to that in the refresh mode, the photoelectric conversion elements PD(1,1) to PD(4096,4096) are set in a state in which charges by photoelectric conversion can be accumulated.

When the X-ray detector 110 is irradiated with X-rays, charges proportional to the X-ray dose are accumulated in the photoelectric conversion elements PD(1,1) to PD(4096, 4096). In addition to the X-ray signal, the photoelectric conversion elements PD(m,n) also have a dark current which is excited by the temperature and flows. Charges by the dark current are also accumulated together with the charges proportional to the X-ray dose.

Charge read will be described next.

In the state in which the potentials of all the common electrodes D are set to the bias potential Vs at the time of photoelectric conversion, the driver 262 turns on all the reset switches 242 to set all the column signal lines Lc1 to Lc4096 to the reset reference potential 241 Vbt. In this state, the driver 262 turns off all the reset switches 242. The driver 262 also turns on the switches SW(1,1) to SW(1,4096) by applying the potential Vgh to the row select line Lr1. Accordingly, the gate electrodes G are connected to the column signal lines Lc1 to Lc4096 at the potential Vbt. However, since charges are accumulated in the photoelectric conversion elements PD(m,n), the potentials of the column signal lines Lc1 to Lc4096 are induced by the charges and shifted from Vbt to Vbt'. The shift amount (Vbt−Vbt') is proportional to the accumulated charge amount. The shift amount (Vbt−Vbt') is amplified by the preamplifiers 246. The outputs from the preamplifiers 246 are sampled and held by the sample-and-hold circuits 248. The outputs from the sample-and-hold circuits 248 are multiplexed by the analog multiplexer 250 along the time axis. The analog output from the analog multiplexer 250 is converted into a digital signal by the A/D converter 252, read out, and output to the image processing apparatus.

By repeating this operation for all the first to 4,096th rows, accumulated charges in all the pixels are read out. At this time, the magnitude relationship between the bias potential Vs of the common electrode D and the potential Vbt or Vbt' of the gate electrode is the same as in accumulating charges.

The accumulated charges include charges proportional to the X-rays and those by the dark current. To read out only the charges proportional to the X-ray dose, charges by the dark current are accumulated again for the same time, read out, and subtracted. To accurately read out the accumulated charges proportional to the X-rays, a driving operation such as removal of charges remaining in the pixels is executed before accumulation. This operation can be replaced with repetitive read driving.

As described with reference to FIG. 2, to cause the X-ray detector 110 to acquire an X-ray image, driving operations such as accumulation and read of an X-ray signal are necessary.

Figure 3:
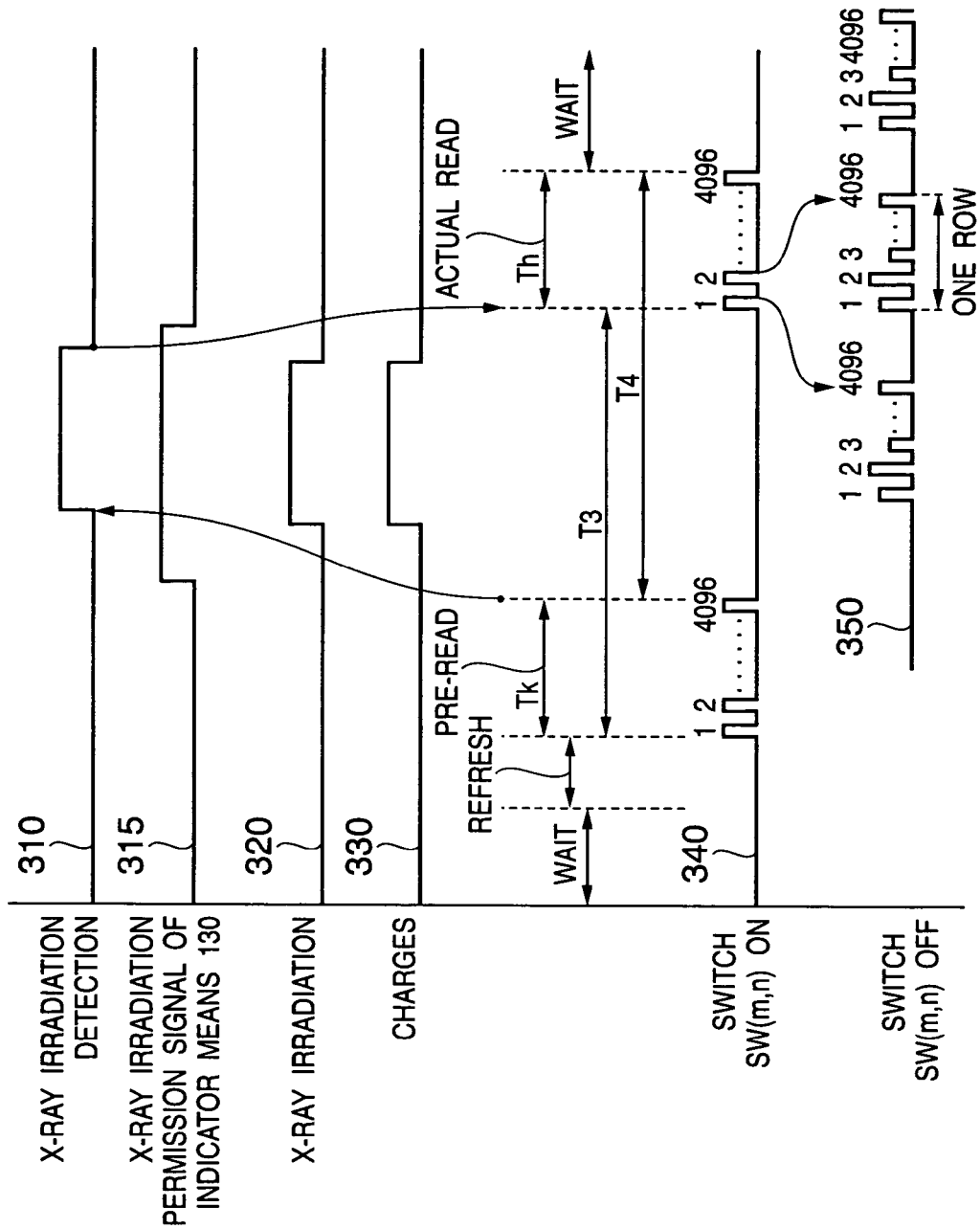
FIG. 3 is a timing chart for explaining synchronization between driving of the X-ray detector 110, control by a detector control unit 120, a recognition signal from a notification unit 130, and X-ray irradiation detection by an X-ray irradiation detection unit 140.

FIG. 3 is a timing chart for explaining synchronization between the detector control unit 120 which controls driving of the X-ray detector 110, the notification unit 130 which generates a recognition signal to notify the radiographer of the driving state of the X-ray detector 110, and the X-ray irradiation detection unit 140 which detects X-rays with which the X-ray detector 110 is irradiated.

The upper convex portion of each signal represents an ON state, and the lower portion represents an OFF state.

Figure 2:
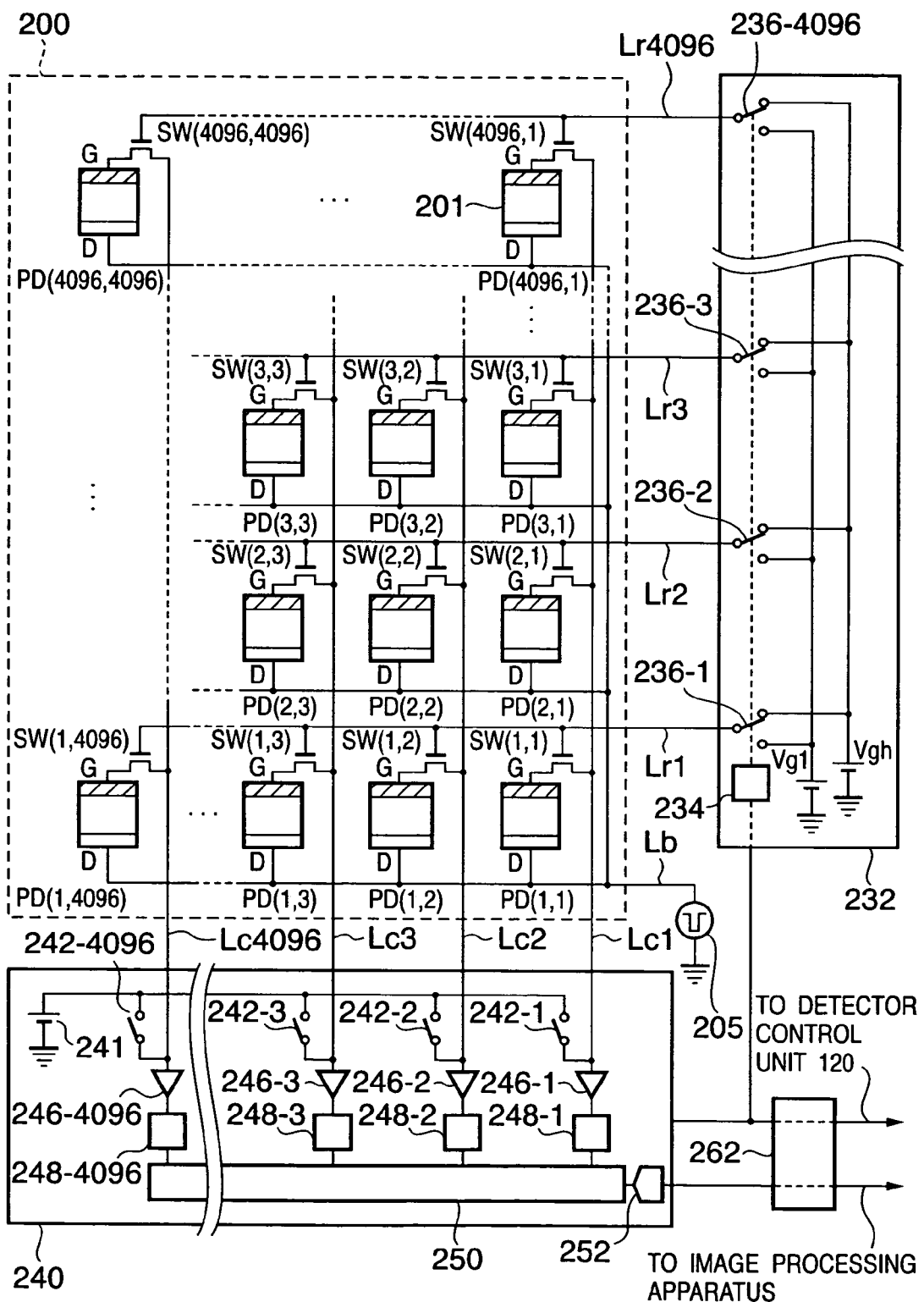
FIG. 2 is a circuit diagram for explaining details of the arrangement and driving of an X-ray detector 110 described in FIG. 1.

Reference numeral 310 denotes detection of X-ray irradiation by the X-ray irradiation detection unit 140; 315, a recognition signal generation state by the notification unit 130; 320, an X-ray irradiation state in which the irradiation button of the X-ray generation apparatus is turned on (automatically or by the radiographer) so that a subject is irradiated with X-rays; 330, charges generated by the photoelectric conversion elements PD(m,n); 340, an ON/OFF state of the switches SW(m,n) corresponding to the switching TFTs in the detector array 200 shown in FIG. 2; and 350, a signal read state of the analog multiplexer 250 in the detector array 200 shown in FIG. 2. As is apparent from the signal read state 350, when the switches SW(m,n) of one row are turned on, charges accumulated in the pixels 201 of one row are read out by the analog multiplexer 250. Driving control of the X-ray detector 110 is done by the detector control unit 120 in accordance with the ON/OFF state 340 and the signal read state 350.

First, the driving start unit 100 applies a voltage to the X-ray detector 110 to start driving. If the X-ray detector 110 requires refresh, the detector control unit 120 first executes refresh after the Wait time. The pre-read in the ON/OFF state 340 indicates a read executed to reset charges that remain after charge removal by refresh. The pre-read time is Tk. The actual read in the ON/OFF state 340 indicates driving for actually reading out accumulated signal charges. The actual read time is Th. The time from the pre-read of the first row to the actual read of the first row is T3. The time from the pre-read of the final row to the actual read of the final row is T4.

As indicated by 340, the switches SW(m,n) are sequentially turned on to read out charges. Hence, the accumulation state shifts between rows. X-ray irradiation can be executed only when all the rows are set in the accumulation state. Hence, the actual X-ray irradiation allowable time is T3−Tk. To allow X-ray irradiation during the time (T3−Tk), the notification unit 130 continuously generates the recognition signal representing permission of X-ray irradiation during the time (T3−Tk).

The OFF state in the recognition signal transmission state 315 also represents a state in which X-ray irradiation is impossible. The radiographer can more easily recognize the X-ray irradiation timing when a recognition signal representing inhibition of X-ray irradiation is generated.

After the actual read, the operation stands by for the Wait time.

The above-described driving including standby for the Wait time, pre-read, accumulation, actual read, and standby for the Wait time is repeatedly executed immediately after the start of driving. This repeat will be referred to as idling driving hereinafter.

The recognition signal representing whether X-ray irradiation is possible is repeatedly generated by the notification unit 130 in accordance with idling driving. The radiographer can irradiate the X-ray detector 110 with X-rays at an appropriate timing on the basis of the recognition signal. Reference numeral 320 denotes the X-ray irradiation state in the accumulation state. At this time, charges are generated in the photoelectric conversion elements PD(m,n), as indicated by 330.

When the X-ray irradiation detection unit 140 is not an X-ray detector, an image read out after X-ray irradiation is compared with an image read out without X-ray irradiation, thereby confirming whether the subject is irradiated with X-rays.

When the X-ray irradiation detection unit 140 is an X-ray detector, the X-ray irradiation start time is detected by the X-ray irradiation detection unit 140, as indicated by 310, so that the signal indicated by 310 is set in the ON state. This signal is sent to the detector control unit 120 so that the X-ray detector 110 is set in the accumulation state during the X-ray irradiation. When X-ray irradiation is ended, the irradiation end time is detected by the X-ray irradiation detection unit 140, and the signal indicated by 310 changes to the OFF state, the actual read indicated by 340 immediately starts.

As described above, when the X-ray irradiation detection unit 140 is an X-ray detector, the accumulation state can be adjusted to the actual X-ray irradiation time. Hence, the accumulation time in idling driving can be set to a time convenient for imaging.

When it is confirmed that the subject is irradiated with X-rays, the above-described driving including standby for the Wait time, pre-read, accumulation, actual read, and standby for the Wait time is executed as in actual X-ray irradiation time, thereby reading out a correction image for dark current correction. When the correction image is subtracted from the image obtained at the time of X-ray irradiation, an image proportional to the X-ray dose can be obtained.

After that, driving of the X-ray detector 110 is stopped. The application voltage for the X-ray detector 110 is dropped, as needed. When the application voltage for the X-ray detector 110 is dropped, power can be saved, and the service life of the X-ray detector 110 increases.

When the X-ray irradiation detection unit 140 is used, X-ray irradiation enable state can be repeated. However, if the X-ray irradiation detection unit 140 is absent, the driving including standby for the Wait time, pre-read, accumulation, actual read, and standby for the Wait time shown in FIG. 3 is executed only once. The radiographer is notified of the X-ray irradiation enable state only once. X-ray irradiation is executed during this time. Accordingly, the necessity of X-ray irradiation detection can be eliminated. In this case, the accumulation time immediately before the actual read equals that immediately before the correction read. Hence, the time can be determined in advance.

As described above, when the X-ray irradiation detection unit 140 which time-serially detects X-ray irradiation is prepared, X-ray irradiation can be determined, and the X-ray detector 110 can be driven without synchronization with the X-ray generation apparatus. When an X-ray detector is used as the X-ray irradiation detection unit 140, the accumulation time can be adjusted to the actual X-ray irradiation time by detecting the irradiation start time and irradiation end time. Hence, the accumulation time in idling driving can be set to a time convenient for imaging. In addition, when the notification unit 130 generates a recognition signal which notifies the radiographer of the accumulation state in which X-ray irradiation is possible or other states, imaging can be executed without synchronization with the X-ray generation apparatus.

Idling driving which repeats the cycle of the recognition signal which notifies the radiographer of the accumulation state in which X-ray irradiation is possible or other states is executed. Accordingly, even when the X-ray irradiation timing is temporarily missed, X-ray irradiation can be executed at an appropriate timing in the next cycle.

Figure 4:
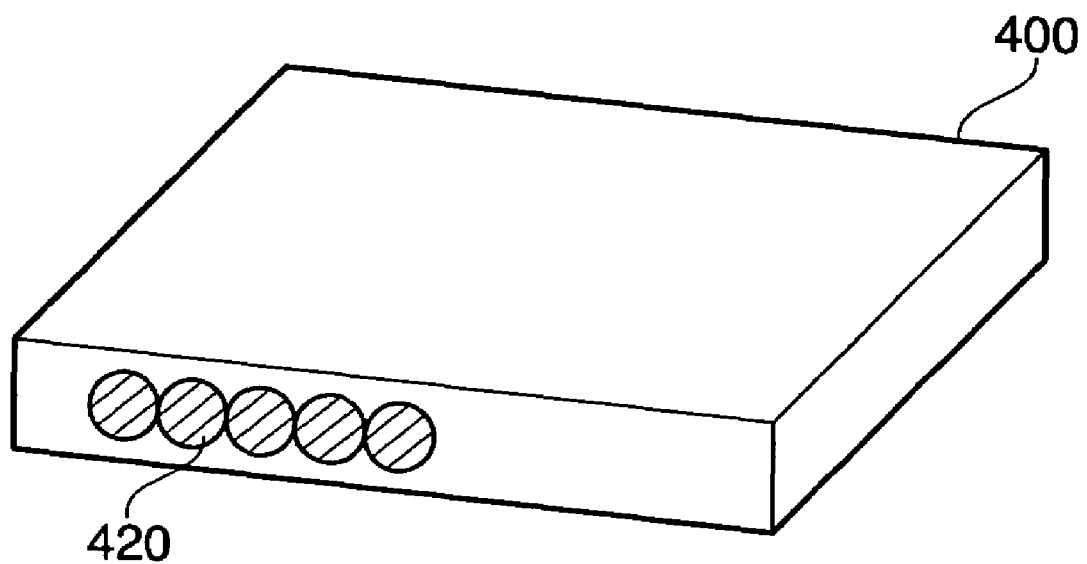
FIG. 4 is a perspective view showing the notification unit 130 using light.

FIG. 4 shows an example in which the recognition signal is generated by the notification unit 130 using light.

A housing 400 houses the X-ray detector 110, detector control unit 120, and X-ray irradiation detection unit 140. A light-emitting unit 420 includes, for example, five LEDs.

The detector control unit 120 controls to generate a recognition signal to cause the LEDs on the housing 400 to emit light.

To distinguish the accumulation state in which X-ray irradiation is possible from other states, for example, five LEDs emit light in the accumulation state in which X-ray irradiation is possible while two LEDs emit light in other states. The radiographer can irradiate a subject with X-rays at an appropriate timing while observing the subject and the light of the LEDs.

Figure 5:
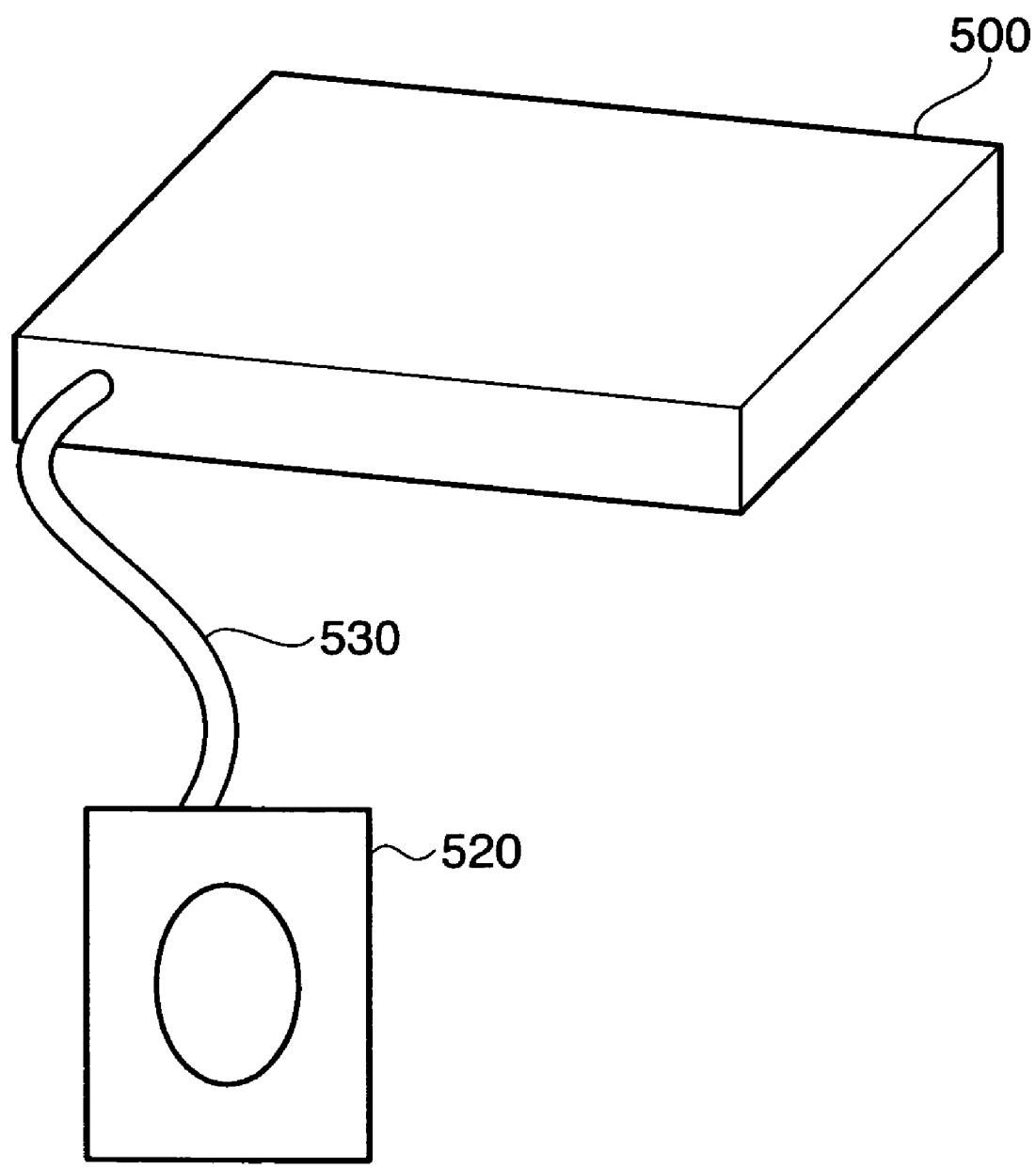
FIG. 5 is a perspective view showing the notification unit 130 using sound.

FIG. 5 shows an example in which a recognition signal is generated by the notification unit 130 using sound.

A housing 500 houses the X-ray detector 110, detector control unit 120, and X-ray irradiation detection unit 140. Reference numeral 520 denotes a speaker; and 530, a communication line to the speaker.

The detector control unit 120 controls to generate a recognition signal so that sound is generated from the speaker 520 through the communication line 530 from the housing 500. To distinguish the accumulation state in which X-ray irradiation is possible from other states, for example, continuous sound is generated in the accumulation state in which X-ray irradiation is possible while pulse sound is generated in other states. The radiographer can irradiate a subject with X-rays at an appropriate timing while observing the subject and listening to the sound.

Figure 6:
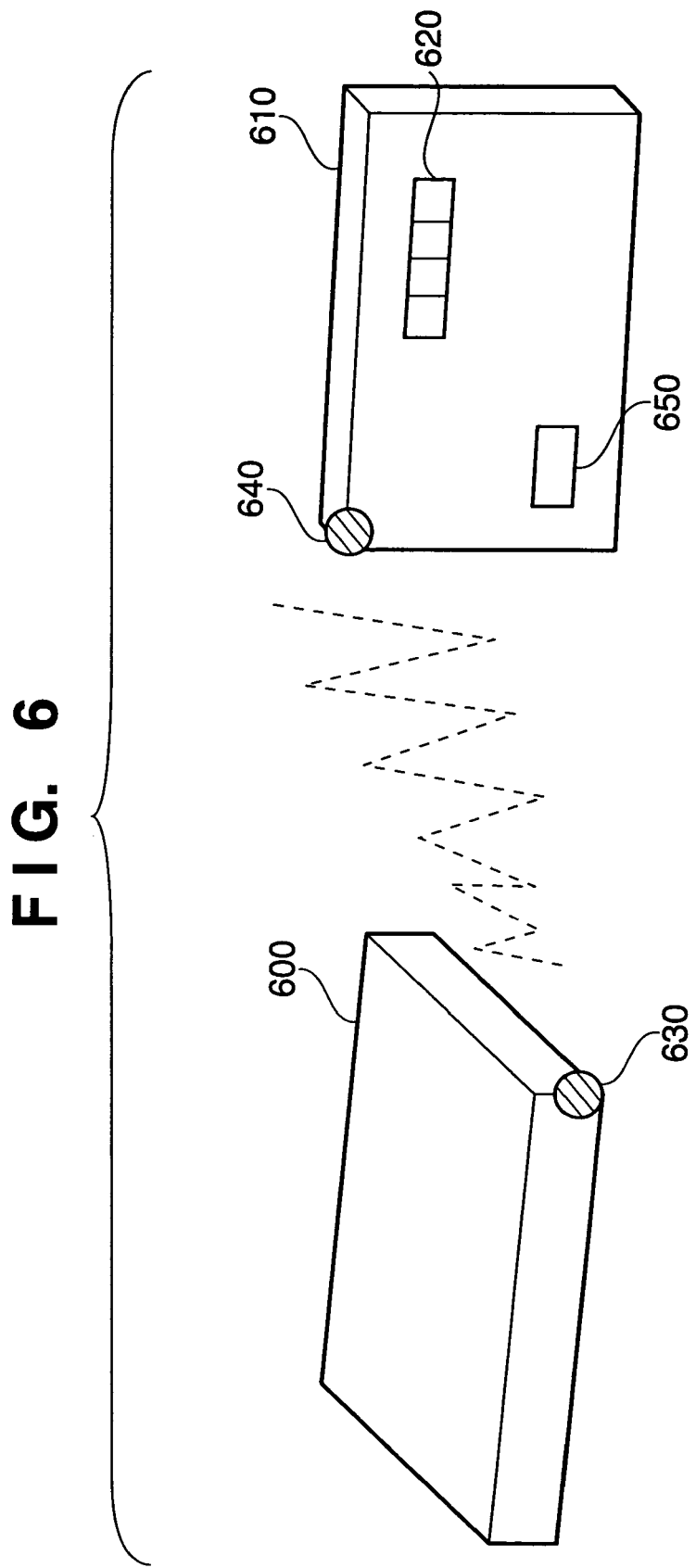
FIG. 6 is a perspective view showing the notification unit 130 using wireless communication.

FIG. 6 shows an example in which a recognition signal is generated by the notification unit 130 using wireless communication.

A housing 600 houses the X-ray detector 110, detector control unit 120, and X-ray irradiation detection unit 140. An OPU 610 transmits imaging information or a signal indicating the start of driving to the housing 600. A light-emitting unit 620 is indicated on the OPU 610. Reference numeral 630 denotes a first wireless communication unit; 640, a second wireless communication unit; and 650, an imaging start button.

When the imaging start button 650 is turned on, the second wireless communication unit 640 in the OPU 610 generates a signal. The first wireless communication unit 630 receives this signal to cause the detector control unit 120 to start driving the X-ray detector 110. This part corresponds to the driving start unit 100 described above. When the X-ray detector 110 starts driving, the detector control unit 120 controls to generate a recognition signal to cause the first wireless communication unit 630 in the housing 600 to generate a signal. The second wireless communication unit 640 receives this signal so that the recognition signal is indicated on the screen of the OPU 610. This part corresponds to the notification unit 130 described above. To distinguish the accumulation state in which X-ray irradiation is possible from other states, for example, indication is done in red in the accumulation state in which X-ray irradiation is possible while indication is done in yellow in other states.

The radiographer can irradiate a subject with X-rays at an appropriate timing while observing the indication and the subject. If the OPU 610 is a compact portable device, a recognition signal may be generated as vibration of the portable OPU 610.

As described above with reference to FIG. 4, the notification unit 130 uses light of LEDs attached to the housing 400 or a radio signal. Accordingly, connection is unnecessary because no synchronization with the X-ray generation apparatus is required, and additionally, the portability of the X-ray detector 110 can further be increased. When the notification unit 130 uses sound, the ears can be concentrated on the recognition signal sound while concentrating the eyes on the subject.

Similarly, when the notification unit 130 uses vibration, imaging can be executed while directing the eyes to the subject and sensing the vibration as the recognition signal on the skin. When the recognition signal is generated as light of the LEDs attached to the housing 400, the subject and the light from the LEDs can easily be recognized because they are located in the same direction.

Figure 7:
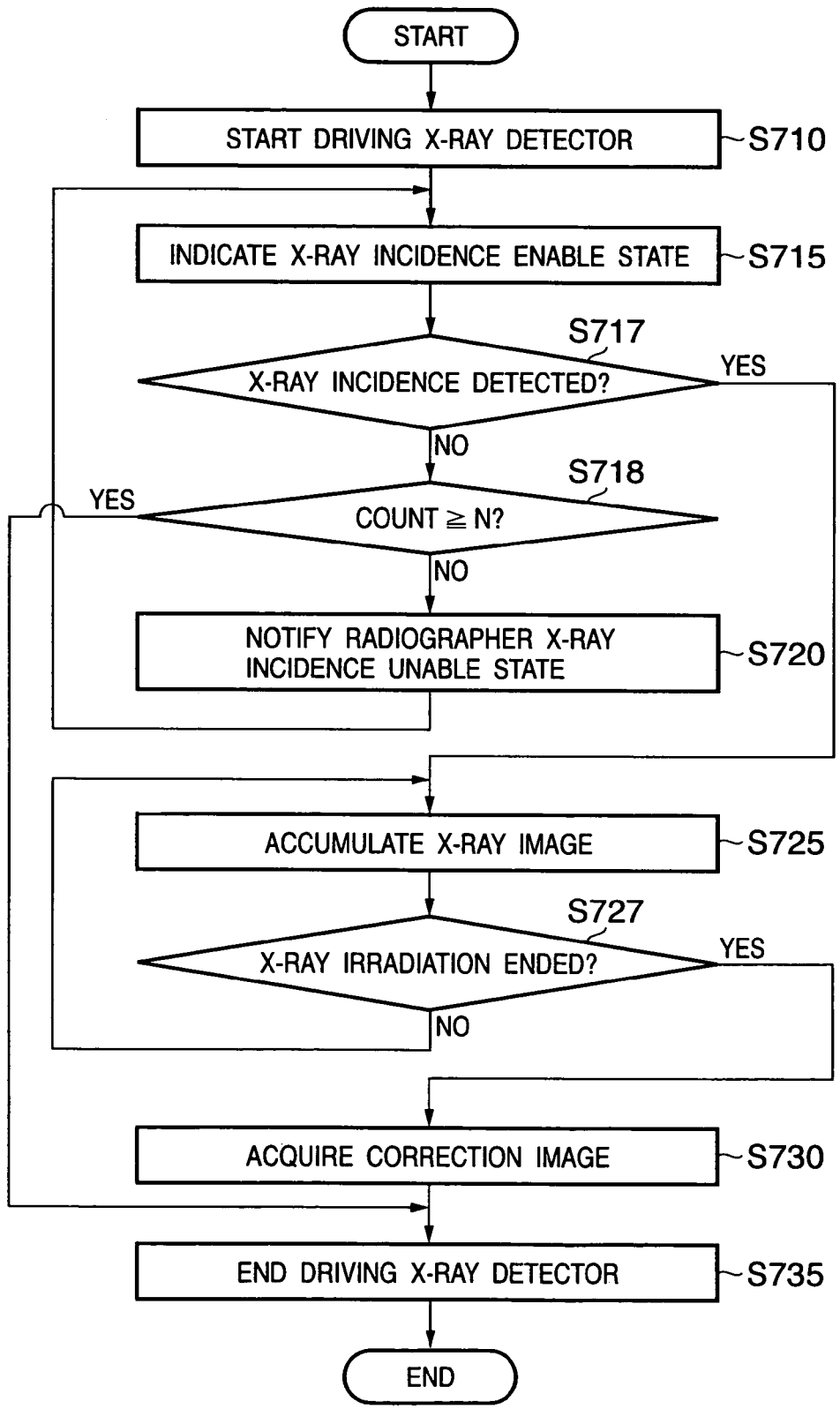
FIG. 7 is a flowchart for explaining a preferred imaging method by the X-ray imaging apparatus according to the first embodiment.

FIG. 7 is a flowchart for explaining the driving flow of the X-ray imaging apparatus in the detector control unit shown in FIG. 1.

A driving start module 710 starts driving the X-ray detector. An X-ray incidence enable state notification module 715 notifies that X-rays can become incident on the X-ray detector. An X-ray incidence detection module 717 detects whether X-rays become incident on the X-ray detector. A count determination module 718 determines the number of times of setting the signal charge accumulation enable state. An X-ray incidence unable state notification module 720 notifies that no X-rays can become incident on the X-ray detector. An X-ray image accumulation module 725 accumulates the signal charges of an X-ray image. An X-ray end detection module 727 detects whether X-ray irradiation on the X-ray detector is ended. A correction image acquisition module 730 acquires an image for correction. A driving end module 735 ends driving the X-ray detector.

First, the driving start unit 100 starts driving the X-ray detector. The driving start module 710 receives a signal from the driving start unit 100 and starts driving the X-ray detector. The predetermined driving operations are executed until the X-ray detector 110 stabilizes. After that, the signal charge accumulation enable state of the X-ray detector 110 is repeated. The X-ray incidence enable state notification module 715 causes the notification unit 130 to generate a recognition signal to notify the radiographer of the accumulation enable state.

When the accumulation enable state is set, and the X-ray generation apparatus irradiates a subject with X-rays, the X-ray incidence detection module 717 detects X-ray incidence on the X-ray detector 110 on the basis of a signal from the X-ray irradiation detection unit 140. When X-ray incidence is detected, the X-ray image accumulation module 725 keeps the X-ray detector 110 set in the signal charge accumulation state. When the X-ray end detection module 727 detects the end of X-ray irradiation, or a predetermined accumulation time has elapsed, accumulation of signal charges is ended.

The X-ray end detection module 727 detects, on the basis of a signal from the X-ray irradiation detection unit 140, that X-ray irradiation on the X-ray detector 110 is ended. Upon detecting the end of X-ray irradiation, the X-ray end detection module 727 notifies the X-ray image accumulation module 725 of the detection. When signal charge accumulation is ended, the correction image acquisition module 730 acquires a correction image to correct the accumulated signal charge image. The correction image is an image acquired by the correction read shown in FIG. 3.

The accumulation time in which the X-ray detector 110 is continuously kept in the signal charge accumulation state is acquired. The correction image is acquired in the same accumulation time. When the correction read is ended, the driving end module 735 ends driving the X-ray detector 110.

If no X-ray irradiation is detected by the X-ray detector 110 even in the accumulation enable state, the count determination module 718 determines the number of times of setting the accumulation enable state or the elapsed time after the start of driving of the X-ray detector 110. When the accumulation enable state has been set a predetermined number of times or more, or a predetermined time or more has elapsed, control is transferred to the driving end module 735 to end driving the X-ray detector 110.

When the number of times has not reached the predetermined value yet, or the elapsed time has not reached the predetermined value yet, the X-ray incidence unable state notification module 720 generates a recognition signal representing that X-ray irradiation is impossible immediately before the X-ray detector 110 is set in the signal charge accumulation unable state. During this time, the X-ray detector 110 executes the pre-read driving. When the X-ray detector 110 is set in the accumulation enable state again, the X-ray incidence enable state notification module 715 causes the notification unit 130 to generate a recognition signal representing the accumulation enable state.

The signal charge accumulation enable state in the driving flow shown in FIG. 7 corresponds to the accumulation state described with reference to FIG. 3. The signal charge accumulation unable state corresponds to the pre-read described with reference to FIG. 3. However, in some cases, since the pre-read driving time is too short, and the signal which is generated during the pre-read to indicate the accumulation unable state is too short, the radiographer cannot recognize it. In such a case, a driving state in which accumulation and pre-read of the X-ray detector 110 are repeated several times is made to correspond to the accumulation unable state.

If an irradiation error occurs, that is X-ray irradiation is done in the accumulation unable state, the X-ray incidence unable state notification module 720 determines the irradiation error on the basis of a signal from the X-ray irradiation detection unit 140 and causes the notification unit 130 to notify that the irradiation error has occurred.

As shown in FIG. 7, when an imaging flow for detecting the presence/absence of X-ray irradiation is prepared, imaging without synchronization with the X-ray generation apparatus can be implemented, and the portability of the X-ray imaging apparatus can be increased.

Figure 8:
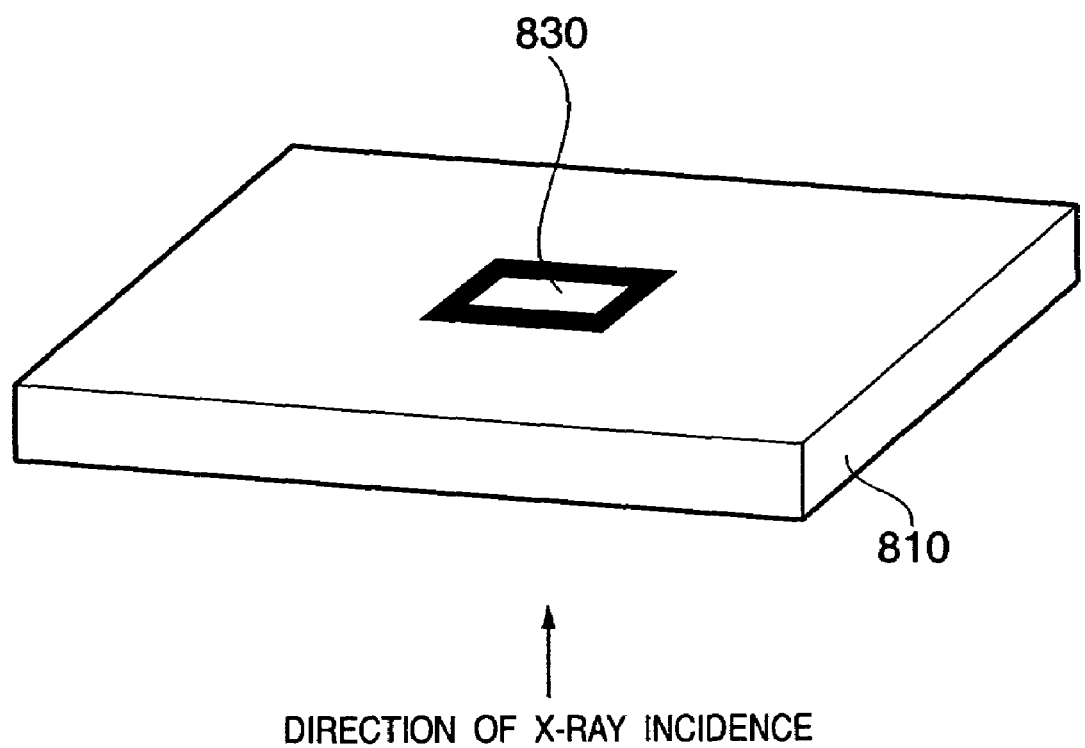
FIG. 8 is a perspective view showing an example of the X-ray irradiation detection unit 140.
Figure 9:
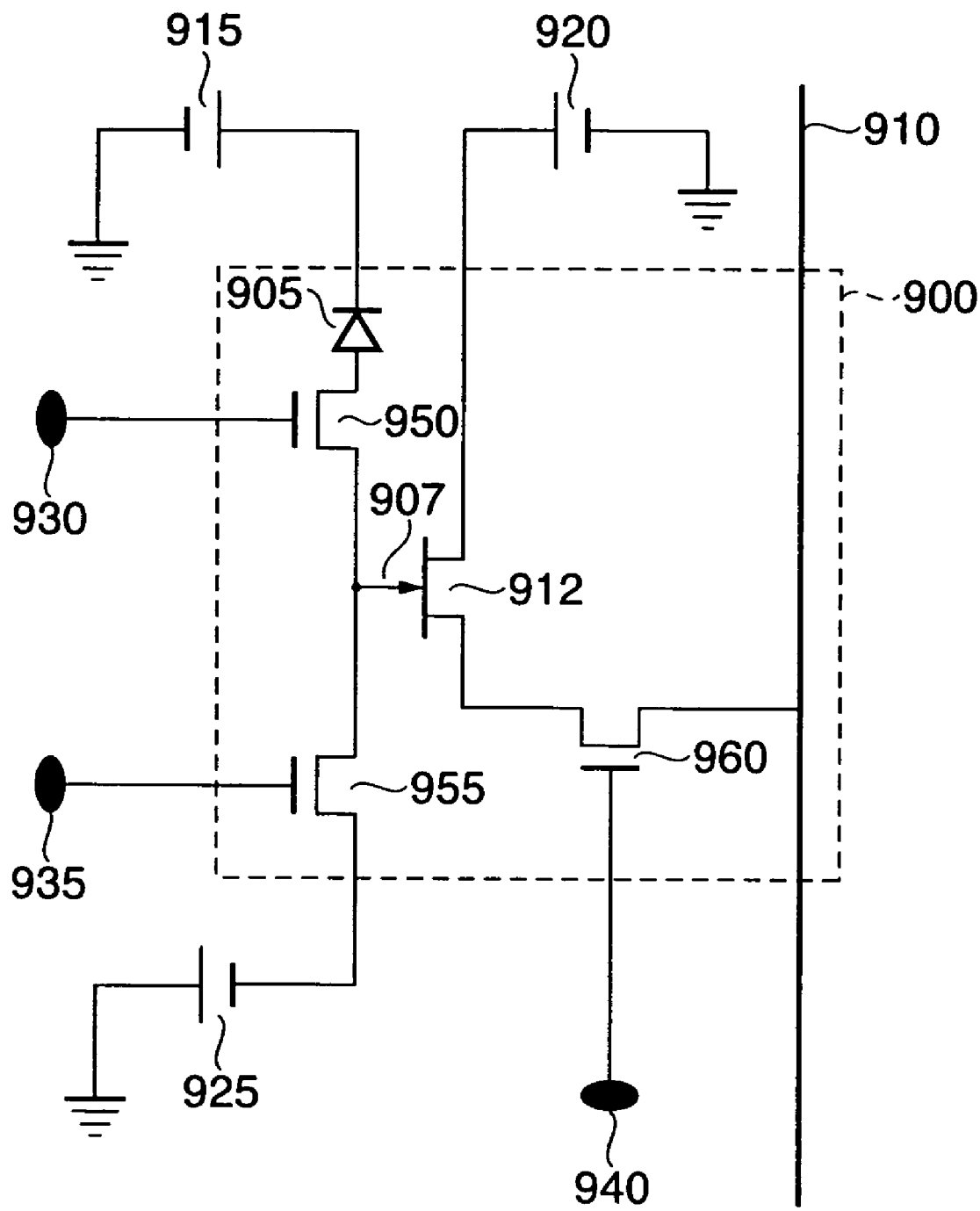
FIG. 9 is a view showing an example in which the X-ray detector 110 has a nondestructive read function.

FIGS. 8 and 9 show detailed examples of the X-ray detector 110 and X-ray irradiation detection unit 140 described with reference to FIG. 1.

In the example shown in FIG. 8, an X-ray irradiation detection unit 830 is arranged on the opposite side of the X-ray incidence side of an X-ray detector 810. The X-ray irradiation detection unit 830 has the same structure as that of the X-ray detector 200 shown in FIG. 2. In the X-ray irradiation detection unit 830, however, the scanning time on the entire surface of the detector is much shorter than in the X-ray detector 810. Hence, the X-ray irradiation detection unit 830 can execute accumulation and read several ten times during X-ray irradiation on the order of several ms. By this detector, time-series measurement can be executed from the start to the end of X-ray incidence on the X-ray detector 810.

When the X-ray irradiation detection unit 830 and X-ray detector 810 are separately arranged, as shown in FIG. 8, the pixel pitch in the X-ray detector 810 must be so small that an X-ray image of a subject can accurately be acquired. However, the X-ray irradiation detection unit 830 can have a large pixel pitch in order to obtain a high scanning speed and very high sensitivity. Hence, the detectors can have structures suitable for their roles. When the X-ray irradiation detection unit 830 is arranged on the opposite side of the X-ray incidence side to detect X-rays that have passed through the X-ray detector 810, X-ray irradiation on the X-ray detector 810 is not impeded. Accordingly, a satisfactory X-ray image can be obtained.

In the example shown in FIG. 9, the X-ray irradiation detection unit 140 is incorporated in the X-ray detector 110, unlike the arrangement shown in FIG. 8 in which the X-ray detector 810 and X-ray irradiation detection unit 830 are prepared as separate detectors. Each pixel of the X-ray detector 110 has part of the function of the X-ray irradiation detection unit 140.

Reference numeral 900 denotes a pixel. A photodiode 905 accumulates, as signal charges, light emitted from phosphor which has absorbed X-rays. An accumulated charge holding unit 907 holds the accumulated signal charges. A signal line 910 transfers an amplified signal by X-rays. An amplification element 912 amplifies the held signal charges. A first common potential 915 provides a bias voltage to the photodiode 905. A second common potential 920 provides an application voltage to the amplification element 912. A third common potential 925 resets the signal charges held by the accumulated charge holding unit 907. First control 930 controls transfer of accumulated charges in the photodiode 905 to the accumulated charge holding unit 907. Second control 935 controls reset of the charges held by the accumulated charge holding unit 907. Third control 940 controls transfer of an amplified signal by the amplification element 912 to the signal line 910. A first switch 950 is turned on/off by the first control 930. A second switch 955 is turned on/off by the second control 935. A third switch 960 is turned on/off by the third control 940.

Driving of this pixel will be described below.

First, the second switch 955 is turned on by the second control 935 to reset the accumulated charge holding unit 907 to the third common potential 925. When the second switch 955 is turned on, the accumulated charge holding unit 907 is set in the floating state while being reset. Next, the first switch 950 is turned on by the first control 930 to transfer signal charges accumulated in the photodiode 905 to the accumulated charge holding unit 907. The potential of the accumulated charge holding unit 907 increases in accordance with the signal charges. When the third switch 960 is turned on by the third control 940, the signal amplified in accordance with the increased potential is output to the signal line.

When the above operation is repeated in the accumulation state of the X-ray detector 110, the signal charges which are transferred from the photodiode 905 to the accumulated charge holding unit 907 and accumulated any time can be read out. When the change in difference before and after the readout signal is checked, the start and end of X-ray incidence on the X-ray detector 110 can be detected.

When the saturation threshold value of signal charges in the accumulated charge holding unit 907 is known in advance, by detecting the signal charges accumulated and held any time, transfer of accumulated charges to the accumulated charge holding unit 907 can be stopped while keeping the second switch 955 in the ON state before the signal charges in the accumulated charge holding unit 907 are saturated.

As described above, in the method of reading out the signal charges transferred from the photodiode 905 to the accumulated charge holding unit 907 and accumulated any time, the signal charges transferred to the accumulated charge holding unit 907 and accumulated can be read out while being stored. Hence, this read method will be called a nondestructive read. By using the nondestructive read and forming the X-ray irradiation detection unit 140 including the read signal differential circuit, the start and end of X-ray incidence on the X-ray detector 110 can be detected without synchronization with the X-ray generation apparatus.

Figure 10:
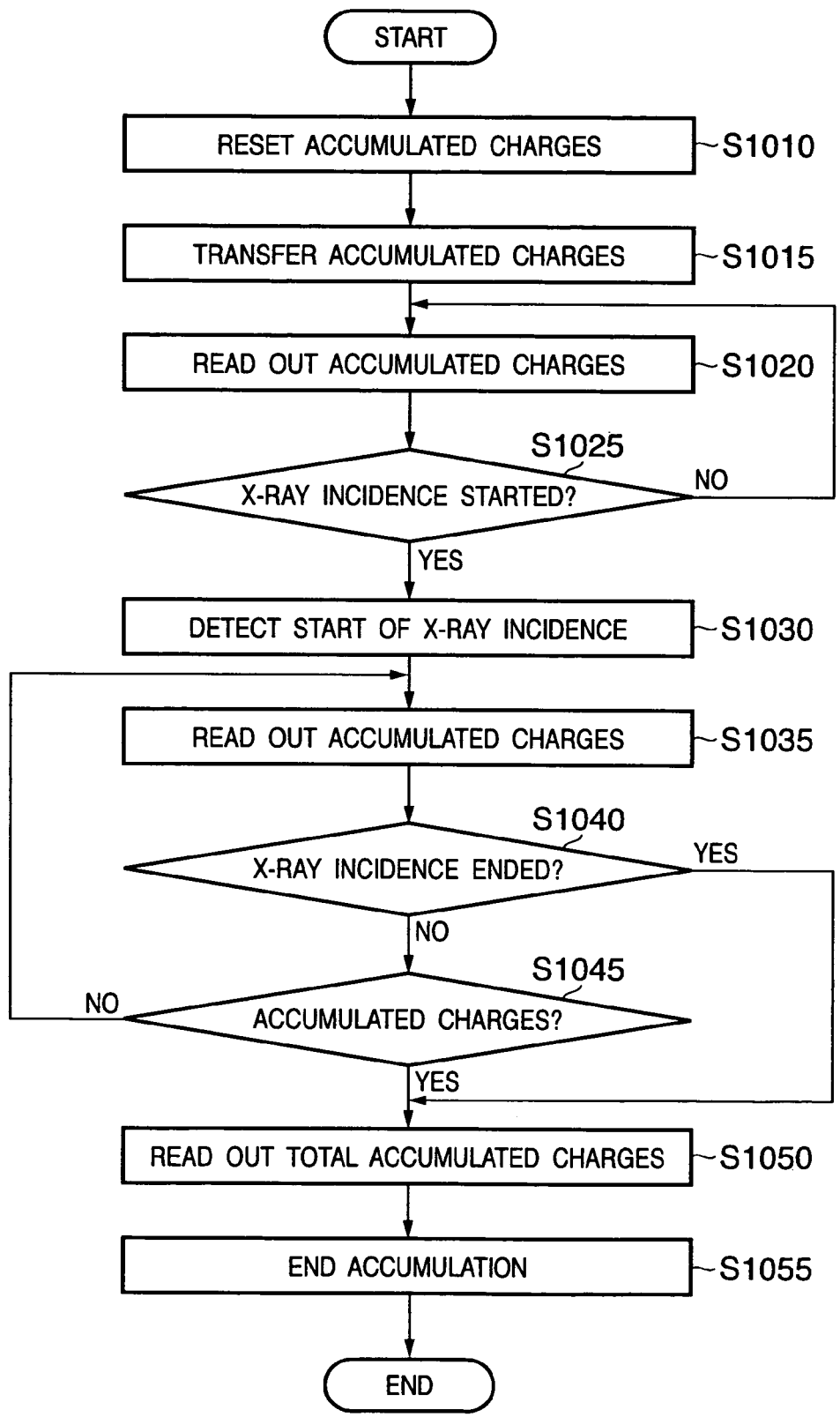
FIG. 10 is a flowchart for explaining the accumulation control method of the X-ray detector 110 using the nondestructive read function.

FIG. 10 is a flowchart for explaining the flow for detecting the start and end of X-ray incidence by using the nondestructive read function.

An accumulated charge reset module 1010 removes charges accumulated in the accumulated charge holding unit 907. An accumulated charge transfer module 1015 transfers accumulated charges from the photodiode 905 to the accumulated charge holding unit 907. A held charge read module 1020 reads out the charges held by the accumulated charge holding unit 907. An incidence start determination module 1025 determines whether the start of X-ray incidence is detected. An X-ray incidence start detection module 1030 transmits the start of X-ray incidence to the detector control unit 120 to reflect it on the driving of the X-ray detector 110. A held charge read module 1035 reads out the charges held by the accumulated charge holding unit 907. An incidence end determination module 1040 determines whether the end of X-ray incidence is detected. An accumulated charge determination module 1045 determines whether the accumulated charge amount has reached a predetermined value. A total accumulated charge read module 1050 reads out the total accumulated charges held by the accumulated charge holding unit 907 to obtain an image. An accumulation end module 1055 ends accumulation by the X-ray detector 110.

First, before charge accumulation by the X-ray detector 110, the accumulated charge reset module 1010 resets charges in the photodiode 905 and those in the accumulated charge holding unit 907. The first switch 950 is turned on by the first control 930 to set the photodiode 905 in the accumulation state.

Next, the accumulated charge transfer module 1015 transfers the charges accumulated in the photodiode 905 to the accumulated charge holding unit 907. After the photodiode 905 is set in the accumulation state again, the held charge read module 1020 reads out the charges held by the accumulated charge holding unit 907. The incidence start determination module 1025 determines the increase in accumulated charges by X-rays by reading out the readout signal and obtaining the difference before and after the read, thereby detecting the start of X-ray incidence. If no X-ray incidence is detected even after the elapse of a predetermined time, the driving of the X-ray detector 110 is ended.

Upon detecting that X-rays are incident, the X-ray incidence start detection module 1030 transmits the start of X-ray incidence to the detector control unit 120 to keep the driving of the X-ray detector 110 in the signal charge accumulation state. While the X-ray detector 110 keeps the accumulation state, the held charge read module 1035 reads out the charges held by the accumulated charge holding unit 907 to monitor the signal charge accumulation state by X-ray incidence. The incidence end determination module 1040 reads out the readout signal and obtains the difference before and after the read, thereby detecting that the X-ray incidence is ended, and the signal charges do not increase any more while monitoring the change in accumulated charges by the X-rays.

When the end of X-ray incidence is detected, the total accumulated charge read module 1050 reads out all the signal charges accumulated and held by the accumulated charge holding unit 907 during X-ray incidence to obtain an X-ray image. When the end of X-ray incidence is not detected, the accumulated charge determination module 1045 determines whether the total accumulated charge amount has reached a predetermined value while monitoring the charge accumulation state.

When it is detected that the total accumulated charge amount has reached a predetermined value, the first switch 950 is kept in the ON state to prevent the accumulated charge holding unit 907 from further accumulating charges. The control is immediately transferred to the total accumulated charge read module 1050.

When the end of X-ray incidence is detected, or it is detected that the total accumulated charge amount has reached a predetermined value, the total accumulated charge read module 1050 is executed. The accumulation end module 1055 ends accumulation by the X-ray detector 110.

As described above, when the X-ray detector 110 capable of executing the nondestructive read is used, no detector which functions as the X-ray irradiation detection unit 140 need be prepared in addition to the X-ray detector 110. Hence, the X-ray detector 110 can have a simpler mechanical structure with a low profile and light weight so that the portability of the X-ray imaging apparatus increases.

Second Embodiment

The second embodiment will be described, in which an X-ray imaging apparatus has a notification unit which notifies a radiographer of the driving state of the X-ray detector so that imaging can be executed without synchronization with the X-ray generation apparatus.

Figure 11:
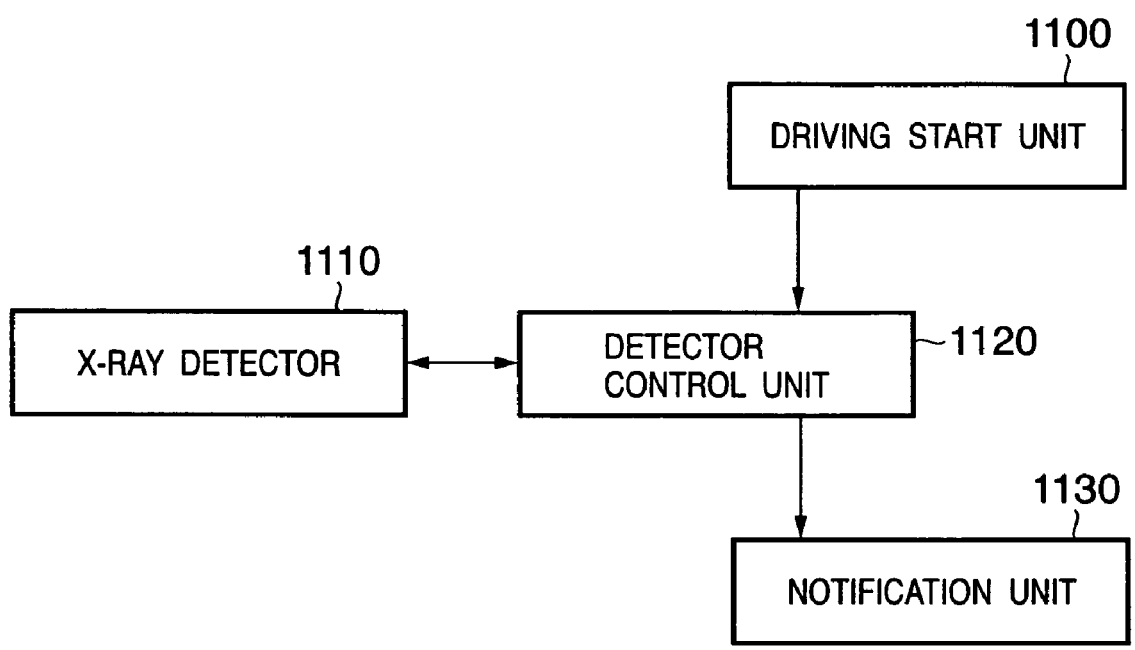
FIG. 11 is a schematic block diagram showing a preferred example of an X-ray imaging apparatus according to the second embodiment.

FIG. 11 is a schematic block diagram showing a preferred example of an X-ray imaging apparatus according to the second embodiment. Reference numeral 1100 denotes a driving start unit (including a device, circuit, program code, and the like, which have the function); 1110, an X-ray detector; 1120, a detector control unit (including a device, circuit, program code, and the like, which have the function); and 1130, a notification unit (including a device, circuit, program code, and the like, which have the function).

First, the driving start unit 1100 sets the X-ray detector 1110 in an imaging enable state. More specifically, the X-ray detector 1110 is powered on, and in this state, driving of the X-ray detector 1110 necessary for imaging is started. This operation is generally implemented by, for example, causing the radiographer to press the imaging button on the OPU that operates the X-ray detector 1110. The X-ray detector 1110 that has started driving is caused to execute predetermined driving operations by the detector control unit 1120. The driving operations include driving for stabilizing the X-ray detector 1110 after voltage application and driving in a state in which the X-ray detector 1110 accumulates an X-ray signal with which a subject is irradiated.

To make the radiographer distinguish the driving (to be referred to as an accumulation state hereinafter) for accumulating the X-ray signal from other driving operations, the notification unit 1130 generates a distinguishable signal. The signal may be a signal by light, a signal by sound, or a signal by vibration.

When a signal by light is used, an LED prepared on the housing of the X-ray detector 1110 is caused to continuously emit light in the X-ray signal accumulation state and blink in another driving state. Alternatively, a notification of the accumulation state may be displayed on the OPU operated by the radiographer. When a signal by sound is used, the X-ray detector 1110 or OPU generates continuous sound in the accumulation state and intermittent sound in another driving state. When a signal by vibration is used, the radiographer carries a portable monitor capable of communicating with the detector control unit 1120 so that he/she can know the accumulation state on the basis of the vibration strength.

When the notification unit 1130 notifies that the X-ray detector 1110 is set in the accumulation state, and the irradiation button of the X-ray generation apparatus is pressed by the radiographer, the driving start unit 1100 accumulates an X-ray signal that has passed through a subject. The detector control unit 1120 executes driving operations for ending the accumulation state of the X-ray detector 1110, acquiring correction data, dropping the voltage, and the like. The detailed operation and driving of the X-ray detector 1110 are the same as in FIG. 2.

As described above, since the radiographer is notified of the driving state of the X-ray detector 1110, he/she can identify that the X-ray detector 1110 is in the accumulation state. Then, the irradiation button of the X-ray generation apparatus is pressed to irradiate a subject with X-rays. Hence, the X-ray detector 1110 need not synchronize with the X-ray generation apparatus. Accordingly, the radiographer can carry the X-ray detector 1110 and execute imaging without minding connection.

In addition, when the irradiation button of the X-ray generation apparatus is pressed to irradiate a subject with X-rays, due to the delay of X-ray irradiation caused by the time required for driving necessary after the irradiation button is pressed until the X-ray detector 1110 is set in the accumulation state, a blur due to the motion of the subject and, for example, a blur around the heart caused by its motion can be eliminated.

Figure 12:
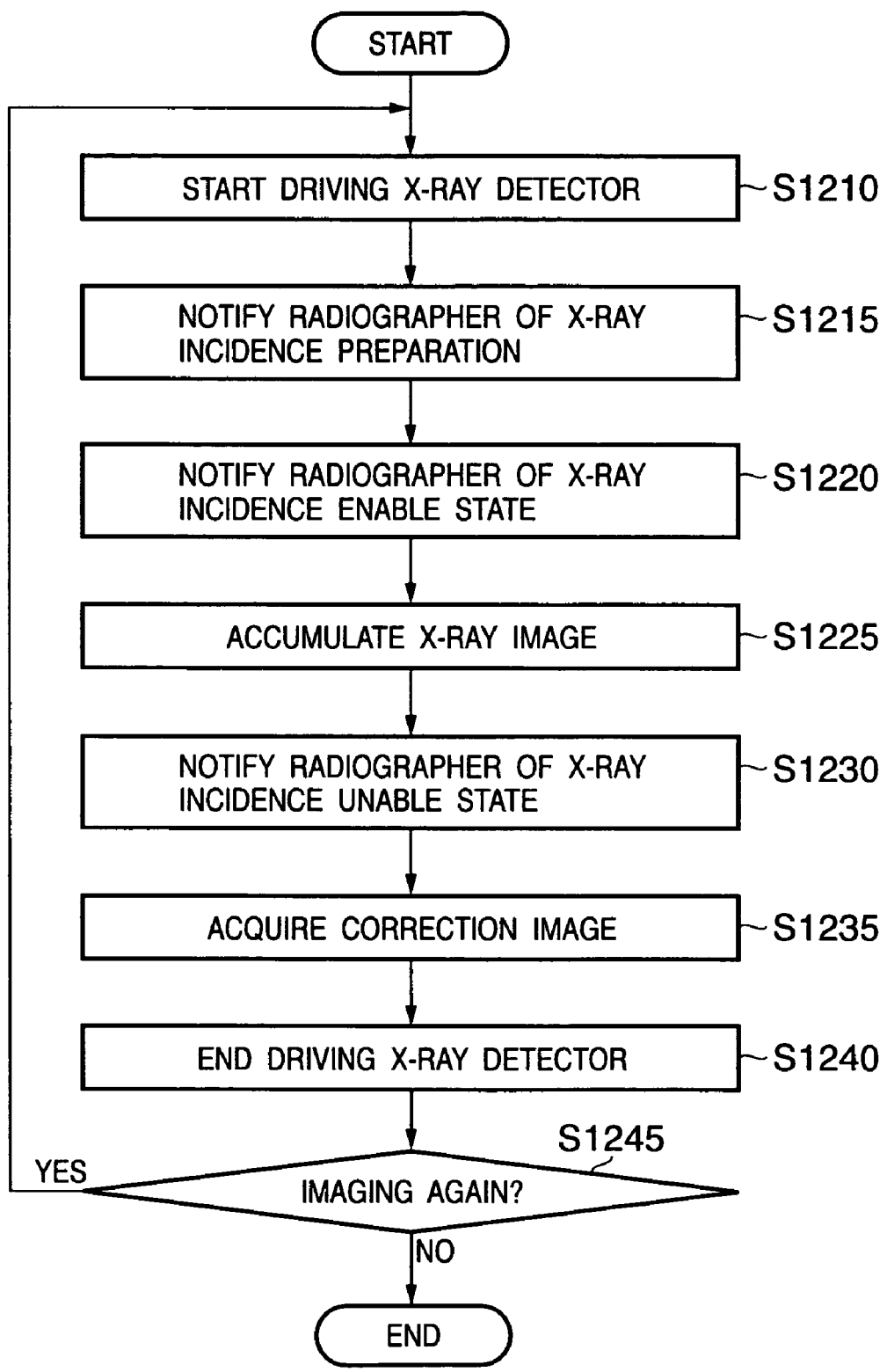
FIG. 12 is a flowchart for explaining a preferred imaging method by the X-ray imaging apparatus according to the second embodiment.

FIG. 12 is a flowchart for explaining the driving flow of the X-ray imaging apparatus in the detector control unit shown in FIG. 11.

A driving start module 1210 starts driving the X-ray detector. An X-ray incidence preparation notification module 1215 notifies the radiographer of the state until the X-ray detector 1110 is set in the X-ray irradiation enable state. An X-ray incidence enable state notification module 1220 notifies that X-rays can become incident on the X-ray detector 1110. An X-ray image accumulation module 1225 accumulates the signal charges of an X-ray image. An X-ray incidence unable state notification module 1230 notifies that no X-rays can become incident on the X-ray detector 1110. A correction image acquisition module 1235 acquires an image for correction. A driving end module 1240 ends driving the X-ray detector. A determination module 1245 determines whether continuous imaging is designated by the driving start unit 1100.

First, the driving start unit 1100 starts driving the X-ray detector. The driving start module 1210 receives a signal from the driving start unit 1100 and starts driving the X-ray detector 1110. The predetermined driving operations are executed until the X-ray detector 1110 stabilizes. Until the driving stabilizes, the X-ray incidence preparation notification module 1215 causes the notification unit 1130 to generate a signal which notifies that the X-ray detector 1110 is in a preparation state.

When the X-ray detector 1110 is set in the accumulation enable state, the X-ray incidence enable state notification module 1220 causes the notification unit 1130 to generate a signal that notifies that X-ray irradiation is possible. This operation is continued until the X-ray detector 1110 ends accumulation. The X-ray image accumulation module 1225 sets the X-ray detector 1110 in the accumulation state simultaneously with the signal from the X-ray incidence enable state notification module 1220 and keeps this state for a predetermined time. After the elapse of a predetermined accumulation time, the X-ray detector 1110 ends signal charge accumulation. After the end of accumulation, the X-ray incidence unable state notification module 1230 causes the notification unit 1130 to generate a signal which notifies that the X-ray detector 1110 is in the accumulation unable state.

When signal charge accumulation is ended, the correction image acquisition module 1235 acquires a correction image to correct the accumulated signal charge image. When acquisition of the correction image is ended, the driving end module 1240 ends driving the X-ray detector 1110.

When continuous imaging is designated by the driving start unit 1100, the determination module 1245 starts driving the X-ray detector 1110 again. When no continuous imaging is designated, the voltage of the X-ray detector 1110 is dropped to set it in a sleep state (power-off state).

The X-ray detector 1110 of certain type cannot continuously accumulate an X-ray image. For example, a detector which cannot completely reset accumulated charges by read driving must always be set in the sleep state after it is set in signal charge accumulation state once.

As shown in FIG. 12, when the imaging flow for generating a signal that can identify that the X-ray detector 1110 is in the preparation state in preparation until the X-ray detector 1110 is set in the X-ray image accumulation state is prepared, even a detector which must be set in the sleep state after signal charges are accumulated once can implement imaging without synchronization with the X-ray generation apparatus. Hence, the portability of the X-ray imaging apparatus can be increased.

Other Embodiment

The present invention is also achieved even by supplying a software program (the modules of the flows shown in FIGS. 7, 10 and 12) which implements the functions of the above-described embodiments to the system or apparatus directly or from a remote site and causing the computer of the system or apparatus to read out and execute the supplied program code. The form need not always be a program as long as the functions of the program can be obtained.

Hence, to implement the functional processing of the present invention by a computer, the program code itself, which is installed in the computer, also implements the present invention. That is, a computer program itself, which implements the functional processing of the present invention, is also incorporated in the claim of the present invention.

In this case, the program can take any form such as a subject code, a program to be executed by an interpreter, or script data to be supplied to the OS as long as the functions of the program can be obtained.

As a recording medium for supplying the program, for example, a floppy disk, hard disk, optical disk, magnetooptical disk, MO, CD-ROM, CD-R, CD-RW, magnetic tape, nonvolatile memory card, ROM, or DVD (DVD-ROM or DVD-R) can be used.

As another program supply method, a client computer may be connected to a homepage on the Internet using a browser in the computer, and the computer program itself of the present invention or a compressed file containing an automatic install function may be downloaded from the homepage to a recording medium such as a hard disk. A program code that constitutes the program of the present invention may be divided into a plurality of files, and the files may be downloaded from different homepages. That is, a WWW server which causes a plurality of radiographers to download a program file that causes a computer to implement the functional processing of the present invention is also incorporated in the claim of the present invention.

The program of the present invention may be encrypted, stored in a storage medium such as a CD-ROM, and distributed to radiographers. Any radiographer who satisfies predetermined conditions may be allowed to download key information for decryption from a homepage through the Internet, execute the encrypted program using the key information, and install the program in the computer.

The functions of the above-described embodiments are implemented not only when the readout program is executed by the computer but also when the OS or the like, which is running on the computer, performs part or all of actual processing on the basis of the instructions of the program.

The functions of the above-described embodiments are also implemented when the program read out from the recording medium is written in the memory of a function expansion board inserted into the computer or a function expansion unit connected to the computer, and the CPU of the function expansion board or function expansion unit performs part or all of actual processing on the basis of the instructions of the program.

The present invention is not limited to the above embodiments and various changes and modifications can be made within the spirit and scope of the present invention. Therefore, to apprise the public of the scope of the present invention, the following claims are made.

What is claimed is:

1. An X-ray imaging apparatus comprising:
   an X-ray detector which detects X-rays irradiated from an X-ray source;
   a detector control unit which controls the X-ray detector to repeatedly execute a charge accumulation of the X-ray detector and execute a charge removal of the X-ray detector before X-rays are irradiated in response to ON-state of an irradiation designation member; and
   a notification unit which notifies an operator of a period to execute the charge accumulation before X-rays are irradiated in response to ON-state of an irradiation designation member by light emitted from a light-emitting unit on a housing of the X-ray detector, from an end of a charge removal of the X-ray detector to a start of a next charge removal of the X-ray detector in accordance with a control of the X-ray detector by the detector control unit.

2. The apparatus according to claim 1, further comprising an X-ray irradiation detection unit which detects a start and/or an end of X-ray irradiation,
   wherein the detector control unit controls the X-ray detector by a detection signal from the X-ray irradiation detection unit.

3. The apparatus according to claim 2, further comprising another X-ray detector which detects the start and/or the end of X-ray irradiation.

4. The apparatus according to claim 2, further comprising a nondestructive read unit in the X-ray detector,
   wherein the start and/or the end of X-ray irradiation is detected on the basis of image data read out nondestructively.

5. The apparatus according to claim 2, wherein when the X-ray irradiation detection unit detects the end of X-ray irradiation, an accumulation time in accumulating the detection signal from the X-ray detector is detected, and the accumulation time is set as an accumulation time for data for dark current correction.

6. The apparatus according to claim 2, wherein an idling cycle of repeating the charge removal and charge accumulation of the X-ray detector is ended at the detection of the start of X-ray irradiation, and the accumulated charges are read out when the X-ray irradiation detection unit detects the end of X-ray irradiation.

7. The apparatus according to claim 1, further comprising a driving start unit which starts driving the X-ray detector and sets the X-ray detector in an accumulation state.

8. The apparatus according to claim 1, wherein the X-ray detector is so driven as to generate an accumulation state for an X-ray image once in one imaging cycle, and before the accumulation state is set, the notification unit notifies in advance that the X-ray detector will be set in the accumulation state.

9. The apparatus according to claim 1, wherein the notification unit generates a signal which distinguishably notifies that the X-ray detector is set in an accumulation state in which X-ray irradiation is possible and that the X-ray detector is set in an accumulation preparation state in which X-ray irradiation is impossible.

10. A processing method for imaging X-rays comprising using an X-ray imaging apparatus having an X-ray detector which detects X-rays irradiated from an X-ray source, the method comprising;
    a detector control step of controlling the X-ray detector to repeatedly execute a charge accumulation of the X-ray detector and execute a charge removal of the X-ray detector before X-rays are irradiated in response to ON-state of an irradiation designation member; and
    a notification step of notifying an operator of a period to execute the charge accumulation before X-rays are irradiated in response to ON-state of an irradiation designation member by light emitted from a light-emitting unit on a housing of the X-ray detector, from an end of a charge removal of the X-ray detector to a start of a next charge removal of the X-ray detector in accordance with a control of the X-ray detector by the detector control step.

11. A processor-readable medium by storing a program for executing a processing method for imaging X-rays by a processor of an X-ray imaging apparatus, having an X-ray detector to detect X-rays irradiated from an X-ray source, the method comprising;
    a detector control step of controlling the X-ray detector to repeatedly execute a charge accumulation of the X-ray detector and to execute a charge removal of the X-ray detector before X-rays are irradiated in response to ON-state of an irradiation designation member; and
    a notification step of notifying an operator of a period to execute the charge accumulation before X-rays are irradiated in response to ON-state of an irradiation designation member by light emitted from a light-emitting unit on a housing of the X-ray detector, from an end of a charge removal of the X-ray detector to a start of a next charge removal of the X-ray detector in accordance with a control of the X-ray detector by the detector control step.

12. An X-ray imaging apparatus comprising:

an X-ray detector which detects X-rays irradiated from an X-ray source;

a detector control unit which controls the X-ray detector to repeatedly execute a charge accumulation of the X-ray detector and execute a charge removal of the X-ray detector before X-rays are irradiated in response to ON-state of an irradiation designation member; and a notification unit which notifies an operator of a period to execute the charge accumulation before X-rays are irradiated in response to ON-state of an irradiation designation member by generating sound or vibration through a wireless communication unit, from an end of a charge removal of the X-ray detector to a start of a next charge removal of the X-ray detector in accordance with a control of the X-ray detector by the detector control unit.

13. An X-ray imaging apparatus comprising:

an X-ray detector which detects X-rays irradiated from an X-ray source;

a detector control unit which controls the X-ray detector to repeatedly execute a charge accumulation of the X-ray detector and execute a charge removal of the X-ray detector before X-rays are irradiated in response to ON-state of an irradiation designation member; and a notification unit which notifies an operator of a period to execute the charge accumulation before X-rays are irradiated in response to ON-state of an irradiation designation member by generating one of sound and vibration through a wired communication unit, from an end of a charge removal of the X-ray detector to a start of a next charge removal of the X-ray detector in accordance with a control of the X-ray detector by the detector control unit.

* * * * *